United States Patent
Kubota et al.

(10) Patent No.: US 7,736,612 B2
(45) Date of Patent: Jun. 15, 2010

(54) PROCESSES FOR PRODUCTION OF SILICA GELS CARRYING DERIVATIZATION AGENTS FOR CARBONYL COMPOUNDS

(75) Inventors: Mamoru Kubota, Osaka (JP); Hitoshi Uemori, Takaraduka (JP)

(73) Assignee: Wako Pure Chemical Industries, Ltd., Osaka-shi (JP)

( * ) Notice: Subject to any disclaimer, the term of this patent is extended or adjusted under 35 U.S.C. 154(b) by 429 days.

(21) Appl. No.: 11/718,960

(22) PCT Filed: Nov. 10, 2005

(86) PCT No.: PCT/JP2005/020614

§ 371 (c)(1),
(2), (4) Date: May 9, 2007

(87) PCT Pub. No.: WO2006/051860

PCT Pub. Date: May 18, 2006

(65) Prior Publication Data

US 2008/0015106 A1    Jan. 17, 2008

(30) Foreign Application Priority Data

Nov. 10, 2004    (JP) ............................. 2004-326530

(51) Int. Cl.
*C01B 33/159* (2006.01)
*G01N 31/00* (2006.01)
(52) U.S. Cl. .................... 423/335; 436/128; 252/181.1; 502/401; 502/405
(58) Field of Classification Search .............. 252/181.1; 423/174, 335; 436/128; 502/401, 405
See application file for complete search history.

(56) References Cited

U.S. PATENT DOCUMENTS 6,436,311 B1    8/2002    Harimoto et al.

FOREIGN PATENT DOCUMENTS

JP    2004-191120 A    7/2004
WO    WO 00/02041 A1    1/2000

OTHER PUBLICATIONS

Jana Slemr, "Determination of volatile carbonyl compounds in clean air," Fresenius Journal of Analytical Chemistry v340 (1991), pp. 672-677.*
Katsushige Takami, Kazuhiro Kuwata, Akiyoshi Sugimae, and Masao Nakamoto, "Trace Determination of Aldehydes in Water by High-Performance Liquid Chromatography," Anal. Chem. 57 (1985), pp. 243-245.*
Shiraishi et al., *J. Environ. Monit.*, 3(6): 654-60 (2001).

* cited by examiner

*Primary Examiner*—Ngoc-Yen M Nguyen
*Assistant Examiner*—Diana J Liao
(74) *Attorney, Agent, or Firm*—Leydig, Voit & Mayer, Ltd.

(57) ABSTRACT

The subject of the present invention is to provide a method for producing a silica gel supporting a derivatizing agent for a carbonyl compound that hardly collects carbonyl compounds during production thereof, and a silica gel supporting a derivatizing agent for a carbonyl compound produced by said production method, in order to lower a blank value in measurement of carbonyl compounds. The present invention also relates to a method for producing a silica gel supporting a derivatizing agent for a carbonyl compound characterized by bringing an acid-supported silica gel into contact with an organic solvent containing the derivatizing agent for a carbonyl compound, a silica gel filler supporting a derivatizing agent for a carbonyl compound comprising the silica gel supporting the derivatizing agent for a carbonyl compound produced by the above production method, a method for producing a silica gel supporting a derivatizing agent for a carbonyl compound characterized by treating in advance a silica gel having a cation-exchange group with the derivatizing agent for a carbonyl compound and then bringing it into contact with an organic solvent containing the derivatizing agent for a carbonyl compound, and the like.

12 Claims, No Drawings

PROCESSES FOR PRODUCTION OF SILICA GELS CARRYING DERIVATIZATION AGENTS FOR CARBONYL COMPOUNDS

TECHNICAL FIELD

The present invention relates to a method for producing a silica gel supporting a derivatizing agent for a carbonyl compound that has a lowered blank value by reducing the amount of carbonyl compounds to be unintentionally collected during production of the silica gel, and a cartridge column filled with the silica gel supporting a derivatizing agent for a carbonyl compound obtained by the production method.

BACKGROUND ART

A method for collecting a carbonyl compound by derivatizing the carbonyl compound with dinitrophenylhydrazine (hereinafter, abbreviated as DNPH) is conventionally used. In particular, a method to use a cartridge for collecting a carbonyl compound filled with a DNPH supported silica gel in the cartridge (column) thereof is usually used. Such a cartridge filled with a DNPH supported silica gel is obtained by passing a solution composed of acetonitrile, DNPH and phosphoric acid through a cartridge filled with a silica gel, as described in, for example, "Compendium Method TO-11A". However, since a mixed solution of DNPH and phosphoric acid reacts easily with carbonyl compounds, this method allows the solution to react with carbonyl compounds in the air upon mixing of acetonitrile, DNPH and phosphoric acid, and further upon charging the mixed solution into a cartridge, resulting in that DNPH is supported by a silica gel with holding the carbonyl compounds collected. There has been a problem, therefore, that because the obtained silica gel has already collected the carbonyl compounds, it has a too high background value (blank value) to be used for high-sensitivity analysis.

For this reason, it has been desired to develop a silica gel supporting a derivatizing agent for a carbonyl compound that has a low background value (blank value), a cartridge (column) filled the silica gel and a production method thereof.

Non-Patent Literature 1: Compendium Method TO-11A

DISCLOSURE OF INVENTION

Problem to be Solved by the Invention

The subject of the present invention is to provide a method for producing a silica gel supporting a derivatizing agent for a carbonyl compound that hardly collects carbonyl compounds during production thereof, and a silica gel supporting a derivatizing agent for a carbonyl compound obtainable by the production method thereof, in order to lower a blank value in measurement of carbonyl compounds.

Means for Solving the Problem

After having intensively studied a way to solve the above problem, the present inventors have found that by bringing an acid-supported silica gel into contact with an organic solvent containing a derivatizing agent for a carbonyl compound, the silica gel supporting the derivatizing agent for a carbonyl compound can be easily obtained, while carbonyl compounds in the air are hardly collected by the silica gel supporting the derivatizing agent for a carbonyl compound. Further, they have found the cartridge blank value of carbonyl compound of a silica gel supporting a derivatizing agent for a carbonyl compound obtained by the production method is 0.06 µg or lower, and have completed the present invention. The present inventors have also found that by treating in advance a silica gel having a cation-exchange group with a derivatizing agent for a carbonyl compound and then bringing it into contact with an organic solvent containing the derivatizing agent for a carbonyl compound, the silica gel supporting the derivatizing agent for a carbonyl compound can be similarly obtained, while carbonyl compounds in the air are hardly collected by the silica gel supporting the derivatizing agent for a carbonyl compound.

Namely, the present invention relates to "a method for producing a silica gel supporting a derivatizing agent for a carbonyl compound characterized by bringing an acid-supported silica gel into contact with an organic solvent containing the derivatizing agent for a carbonyl compound", "a cartridge column filled with a silica gel supporting a derivatizing agent for a carbonyl compound wherein a cartridge blank value of a carbonyl compound is 0.06 µg or lower", "a silica gel filler supporting a derivatizing agent for a carbonyl compound composed of a silica gel supporting a derivatizing agent for a carbonyl compound manufactured by the above production method", "a column for collecting carbonyl compounds filled with the above filler", "a kit for measuring carbonyl compounds composed of the above column, acetonitrile, a column for separating carbonyl compounds, and an eluent for separating carbonyl compounds", and "a method for producing a silica gel supporting a derivatizing agent for a carbonyl compound characterized by treating in advance a silica gel having a cation-exchange group with a derivatizing agent for a carbonyl compound and then bringing it into contact with an organic solvent containing the derivatizing agent for a carbonyl compound".

EFFECT OF THE INVENTION

In conventional methods for producing a silica gel supporting a derivatizing agent for a carbonyl compound, between the time when phosphoric acid and a derivatizing agent for a carbonyl compound such as DNPH and the like (hereinafter, may be abbreviated as DNPH and the like) are mixed and the time when the mixed solution and a silica gel are reacted, the DNPH and the like react with carbonyl compounds in the air to collect them. In contrast, in the production method of present invention where an acid-supported silica gel is brought into contact with DNPH and the like, the contact with air can be mostly avoided resulting in reduction of the amount of the carbonyl compounds collected during production because the DNPH and the like, the acid and the silica gel react at the same time. The silica gel supporting a derivatizing agent for a carbonyl compound obtained by the production method of the present invention, therefore, contains less amount of carbonyl compounds collected during production and has a lower blank value in measurement compared with those manufactured by conventional methods and thus enables to measure a trace of a carbonyl compound.

Further, a silica gel supporting a derivatizing agent for a carbonyl compound manufactured by treating in advance a silica gel having a cation-exchange group with the derivatizing agent for a carbonyl compound and then bringing it into contact with an organic solvent containing the derivatizing agent for a carbonyl compound has a lower blank value in measurement and thus enables to measure a trace of a carbonyl compound, because the cation-exchange group has the same effect as the above acid and the carbonyl compounds collected during production contain less amount compared with those manufactured by conventional methods.

BEST MODE FOR CARRYING OUT THE INVENTION

The carbonyl compound related to the present invention includes any compound having a carbonyl group, and specifically, aldehydes such as formaldehyde, acetaldehyde, benzaldehyde, propionaldehyde, butylaldehyde, acrolein and the like, and ketones such as acetone and methyl ethyl ketone and the like. Among these, formaldehyde, acetaldehyde, acetone and the like which are present in the air with high possibility are particularly preferable.

The acid in the acid-supported silica gel related to the present invention includes any acid that is soluble in water and can be supported in a solid state by a silica gel, and specifically, for example, metaphosphoric acid, boric acid, sulfamic acid, tartaric acid and phthalic acid. Among these, metaphosphoric acid, boric acid, sulfamic acid and tartaric acid are preferable, and metaphosphoric acid is particularly preferable. In addition, the above acid is more preferably not soluble or hardly soluble in the organic solvent of an organic solvent containing a derivatizing agent for a carbonyl compound. Whether an acid is not soluble or hardly soluble in an organic solvent depends on the organic solvent to be used. For example, in the case of acetonitrile (to be described in detail later) which is preferable as an organic solvent, any acid given above as specific examples can be used and among these, metaphosphoric acid is preferable.

The silica gel to be used for preparing the acid-supported silica gel related to the present invention may be prepared by a known method or obtained commercially. Among these, preferably, a silica gel has a shape of a flake or a sphere of 30 to 1,000 μm, preferably, 50 to 500 μm in diameter. A commercially available silica gel includes specifically, for example, Wakogel C-100 (Manufactured by Wako Pure Chemical Industries, Ltd.) and Wakogel C-200 (Manufactured by Wako Pure Chemical Industries, Ltd.).

The supported amount of the acid in the acid-supported silica gel related to the present invention is usually 0.05 to 0.5 g, preferably 0.1 to 0.3 g relative to 1 g of the silica gel. The production method thereof may be carried out by a known method for supporting physically on a silica gel. Specifically, for example, such an above described silica gel is immersed in an aqueous solution dissolving an acid, if necessary under stirring, for usually 30 minutes to 2 hours, preferably 1 to 2 hours and then taken out from the solution followed by drying at usually 50 to 120° C. by, for example, a vacuum dryer. In addition, acid concentration in an aqueous solution dissolving an acid is usually 0.1 to 1.0 g/mL, preferably 0.2 to 0.6 g/mL.

It is particularly preferable to use a silica gel treated in advance with a derivatizing agent for a carbonyl compound (an acid-supported silica gel treated with a derivatizing agent for a carbonyl compound) as an acid-supported silica gel because it can lower a blank value in measurement of carbonyl compounds. This mechanism is not clear, but is considered as follows. Namely, when an acid-supported silica gel is treated in advance with a derivatizing agent for a carbonyl compound, a carbonyl compound adsorbed by the silica gel or acid-supported silica gel reacts with the derivatizing agent for a carbonyl compound and the reaction product (derivatized substance) is supported (held) on the acid-supported silica gel. It is considered that when the obtained acid-supported silica gel treated with the derivatizing agent for a carbonyl compound is subjected to the method for producing a silica gel supporting a derivatizing agent for a carbonyl compound of the present invention, the above derivatized substance is liberated from the acid-supported silica gel because it dissolves in an organic solvent containing the derivatizing agent for a carbonyl compound. It is considered that the carbonyl compound adsorbed in a silica gel and the like can be removed by treating in advance an acid-supported silica gel with a derivatizing agent for a carbonyl compound resulting in lowering a blank value.

The amount of a derivatizing agent for a carbonyl compound supported by an acid-supported silica gel treated with the derivatizing agent for a carbonyl compound is usually 0.01 to 0.2 mg, preferably 0.1 to 0.2 mg relative to 1 g of the silica gel.

The method for treating in advance an acid-supported silica gel with a derivatizing agent for a carbonyl compound is carried out by, for example, immersing the above obtained acid-supported silica gel in a solution containing the derivatizing agent for a carbonyl compound for usually 30 minutes to 2 hours, preferably 1 to 2 hours and then drying. In addition, the concentration of a derivatizing agent for a carbonyl compound in a solution containing the derivatizing agent for a carbonyl compound may be set at usually 0.02 to 0.4 mg/mL, preferably 0.2 to 0.4 mg/mL. Water, methanol, ethanol and acetonitrile are preferable as the solvent to be used for preparing the solution, and water is particularly preferable among these. In addition, in the above method for producing an acid-supported silica gel, for example, the silica gel may be treated by making coexistence with further dissolving a derivatizing agent for a carbonyl compound into a solution dissolving an acid to immerse a silica gel, namely, by bringing the silica gel into contact with a mixed solution of the acid and the derivatizing agent for a carbonyl compound. In view of easiness of production, this method is preferable to the above described method. Specifically, for example, a silica gel is immersed in an aqueous solution dissolving an acid and a derivatizing agent for a carbonyl compound, if necessary under stirring, for usually 30 minutes to 2 hours, preferably 1 to 2 hours and then taken out from the solution followed by drying at usually 50 to 120° C., for example, by a vacuum dryer. The concentration of the acid in the solution dissolving the acid and the derivatizing agent for a carbonyl compound in said method may be set according to the concentration described in the above method for producing the acid-supported silica gel. The concentration of the derivatizing agent for a carbonyl compound may be set so as to be the same as the concentration of the derivatizing agent for a carbonyl compound described in the above treating method. The derivatizing agent for a carbonyl compound to be used in these methods may be either purified or crude.

The derivatizing agent for a carbonyl compound related to the present invention includes amino compounds such as O-substituted hydroxylamines such as O-(2,3,4,5,6-pentafluorobenzyl)hydroxylamine; arylhydrazines such as 4-nitrophenylhydrazine, dinitrophenylhydrazine (DNPH), 4-carboxyphenylhydrazine, phenylhydrazine, diphenylhydrazine and 2-naphthylhydrazine; sulfonylhydrazines such as 4-nitrobenzenesulfonylhydrazine; acylhydrazines such as benzoylhydrazine, 4-nitrobenzoylhydrazine, 4-chlorobenzoylhydrazine, 3-chlorobenzoylhydrazine and 4-bromobenzoylhydrazine; and semicarbazides such as phenylsemicarbazide, tolylsemicarbazide, 3,5-dinitrophenylsemicarbazide, 1-naphthylsemicarbazide and 2-naphthylsemicarbazide. Among these, arylhydrazines such as 4-nitrophenylhydrazine, DNPH, 4-carboxyphenylhydrazine, phenylhydrazine, diphenylhydrazine and 2-naphthylhydrazine are preferable. Among them, DNPH having excellent derivatizing ability is preferable, and among DNPH, 2,4-DNPH is particularly preferable.

The organic solvent of an organic solvent containing a derivatizing agent for a carbonyl compound of the present invention may be a solvent that dissolves the derivatizing agent for a carbonyl compound and selected as appropriate according to the kind of the derivatizing agent for a carbonyl compound. The organic solvent includes specifically, for example, aliphatic hydrocarbons such as hexane; alicyclic hydrocarbons such as cyclohexane; aromatic hydrocarbons such as benzene and toluene; alcohols such as methanol and ethanol; halogenated hydrocarbons such as chloroform and methylene chloride; and acetonitrile. Among these, methanol and acetonitrile are preferable, and acetonitrile is particularly preferable. Acetonitrile is particularly preferable when DNPH is used, since it has high solubility for DNPH which is a desirable example of the above agents for derivatizing a carbonyl compound, especially for 2,4-DNPH.

The method for producing a silica gel supporting a derivatizing agent for a carbonyl compound of the present invention is carried out by bringing an acid-supported silica gel related to the present invention into contact with an organic solvent containing the derivatizing agent for a carbonyl compound related to the present invention. Specifically, for example, an organic solvent containing a derivatizing agent for a carbonyl compound is filled in a container such as a cartridge column filled with an acid-supported silica gel and further flowed therethrough if necessary, and then a gas such as nitrogen gas and air is blown to discharge an excess organic solvent followed by drying. The amount of a derivatizing agent for a carbonyl compound in a silica gel supporting the derivatizing agent for a carbonyl compound of the present invention obtained by the method is usually 0.5 to 5 mg, preferably 1.0 to 3.0 mg relative to 1 g of the silica gel.

The derivatizing agent for a carbonyl compound to be used in the above production method of the present invention may be any agent that is given in the above specific examples, but preferably is purified one. The purification method may be carried out by a known method, for example, a recrystallization method. The container to be used for bringing an acid-supported silica gel into contact with an organic solvent containing a derivatizing agent for a carbonyl compound is preferably a sealed container. The sealed container is specifically a container that enables an organic solvent containing a derivatizing agent for a carbonyl compound to be flowed therethrough without entering of outside air when bringing an acid-supported silica gel into contact with the organic solvent containing a derivatizing agent for a carbonyl compound, and also enables the silica gel to be blown and dried by a gas to be used for discharging the organic solvent without entering of outside air, and further enables sealed storage after drying. More specifically, for example, a cartridge column usually used in this field is included. The factors to increase a blank value of a silica gel can be reduced by preventing the outside air, which usually contains carbonyl compounds, from entering when thus bringing an acid-supported silica gel into contact with an organic solvent containing a derivatizing agent for a carbonyl compound, and by preserving the obtained silica gel supporting a derivatizing agent for a carbonyl compound of the present invention under a sealed condition. In addition, the above outside air means air in an ordinary environment that involves a risk of containing carbonyl compounds. Hereinafter, outside air has the same meaning. Also, the air, nitrogen gas and the like blown through the container after bringing an acid-supported silica gel into contact with an organic solvent containing a derivatizing agent for a carbonyl compound are preferably a gas which is removed carbonyl compounds. Removing the carbonyl compounds may be carried out, for example, by blowing the gas through a collecting column for carbonyl compounds. The collecting column for carbonyl compounds to be used here may be any of a commercially available one, a fabricated one by a known method and a collecting column of the present invention.

The concentration of a derivatizing agent for a carbonyl compound in an organic solvent containing the derivatizing agent for a carbonyl compound in the above production method of the present invention is usually 0.3 to 3.0 mg/mL, preferably 0.6 to 2.0 mg/mL.

In the production method of the present invention, the amount of the organic solvent containing a derivatizing agent for a carbonyl compound, which an acid-supported silica gel is brought into contact with, is usually 2 to 40 mL, preferably 5 to 25 mL and more preferably 5 to 15 mL relative to 1 g of the acid-supported silica gel. Also, the flow rate at which the solvent is flowed is usually 1 to 20 mL/minute, preferably 1 to 10 mL/minute, although it depends on the size of a sealed container to be used.

Drying in the production method of the present invention may be carried out at usually 5 to 40° C. preferably 15 to 30° C. under a pressure of usually 0.01 to 0.3 kPa, preferably 0.01 to 0.1 kPa.

A more specific production method of the present invention will be described in detail as follows, taking as an example the case where 2,4-DNPH is used as a derivatizing agent for a carbonyl compound and acetonitrile is used as an organic solvent.

First, a cartridge column is filled with 0.5 to 1 g of an acid-supported silica gel, and then usually 5 to 20 mL, preferably to 10 mL of acetonitrile containing 2,4-DNPH is filled the cartridge column and further flowed therethrough usually at a rate of 1 to 20 mL/minute for 1 to 20 minutes. Afterward, for example, nitrogen gas or the like is blown to discharge excess acetonitrile and then the silica gel in the cartridge column is dried at usually 10 to 50° C., if necessary under reduced pressure, to obtain the 2,4-DNPH supported silica gel, that is, the silica gel supporting a derivatizing agent for a carbonyl compound of the present invention. In addition, the nitrogen gas or the like to be used here is preferably a gas that has passed through a column for collecting carbonyl compounds.

The cartridge column filled with the silica gel supporting a derivatizing agent for a carbonyl compound of the present invention has a cartridge blank value of usually 0.06 µg or lower, preferably 0.04 µg or lower and more preferably 0.02 µg or lower. In addition, the cartridge blank value indicates the amount of each carbonyl compound contained in one cartridge column, and the lower value enables higher-sensitive analysis. The "cartridge blank value of X g or lower" means here that any of each blank value for formaldehyde, acetaldehyde and acetone, which are typical carbonyl compounds, is "X g or lower". The cartridge column is not particularly limited as long as it can be sealed against outside air and is usually used in this field. The size of a cartridge column is not particularly limited, but is usually 2 to 20 cm, preferably 2 to 10 cm in length, and usually 5 to 50 mm, preferably 10 to 30 mm in diameter. A cartridge column with too large size is not suitable because it is necessary to prevent a silica gel supporting a derivatizing agent for a carbonyl compound from contacting outside air. The cartridge column may have a smaller tube in diameter than the column attached to the top and/or bottom of the column like a syringe or a hypodermic syringe, and in this case, the total length including the smaller tube may be in the above range. The material of a cartridge column is not particularly limited as long as it is usually used in this field, and specifically includes stainless steel and polyethylene. Polyethylene is particularly preferable. The silica gel supporting a derivatizing agent for a carbonyl compound in the cartridge column filled with the silica gel supporting the derivatizing agent for a carbonyl compound of the present invention is the one produced by the above method of the present invention.

The silica gel filler supporting a derivatizing agent for a carbonyl compound of the present invention is obtained by the above production method of the present invention. The amount of the filler to be filled in a cartridge column depends on the size of the cartridge column to be used, but is usually 0.1 to 10 g, preferably 0.1 to 5 g and more preferably 0.1 to 1.0 g. The amount of a derivatizing agent for a carbonyl compound contained in the filler is usually 0.1 to 50 mg, preferably 0.5 to 10 mg and more preferably 0.5 to 5 mg. The cartridge column filled with the silica gel filler by the above charge amount has the above cartridge blank value, that is, a cartridge blank value of usually 0.06 µg or lower, preferably 0.04 µg or lower and more preferably 0.02 µg or lower. The column for collecting carbonyl compounds of the present invention is a cartridge column filled with the silica gel filler supporting a derivatizing agent for a carbonyl compound of the present invention. In addition, the cartridge column to be used as a cartridge column filled with a silica gel filler supporting a derivatizing agent for a carbonyl compound of the present invention includes the same one as the one described in the above paragraph on the cartridge column filled with a silica gel supporting a derivatizing agent for a carbonyl compound of the present invention.

The kit for measuring carbonyl compounds of the present invention is composed of the above column filled with a silica gel filler supporting a derivatizing agent for a carbonyl compound, a column for separating carbonyl compounds and an eluent for separating carbonyl compounds and is preferably a kit for separating and measuring to be used for HPLC. The above column for separating carbonyl compounds may be a column for separating carbonyl compounds to be usually used in this field and includes, for example, a column filled with a silica gel having an octadecyl group (ODS column), and Wakosil DNPH II (manufactured by Wako Pure Chemical Industries Ltd.) as a commercially available product. Also, the eluent for separating carbonyl compounds may be an eluent for separation to be usually used in this field and includes specifically acetonitrile, methanol and water and further a mixture of 2 or more of above solvents, preferably a mixed solution of acetonitrile and water and a mixed solution of methanol and water.

The cation-exchange group in a silica gel having a cation-exchange group related to the present invention may be any of known cation-exchange group and specifically includes, for example, a carboxyl group, a sulfonic acid group, a phosphoric acid group and a phosphonic acid group, and among these a carboxyl group and a sulfonic acid group are preferable.

The silica gel having a cation-exchange group related to the present invention may be either a commercially available one or a prepared one according to a known method. The known method includes, for example, a method where such the above ion-exchange group is chemically bound to a silanol group in a silica gel, for example, by bringing a silica gel into contact with a silane-treating agent having an ion-exchange group, or, for example, by bringing a silica gel into contact with a treating agent having a modified group into which an ion-exchange group can be introduced. Specifically, in the case where the ion-exchange group is, for example, a carboxyl group, a silica gel is immersed in a silane-treating agent having a vinyl group and then oxidized with potassium permanganate to introduce the carboxyl group. In the case where the ion-exchange group is a sulfonic acid group, a silica gel is immersed in a silane-treating agent having an epoxy group and then subjected to an addition reaction with sodium hydrogensulfite to introduce the sulfonic acid group. In addition, the silica gel to be used here includes the same one as the silica gel to be used for manufacturing the above acid-supported silica gel.

The method for producing a silica gel supporting a derivatizing agent for a carbonyl compound of the present invention using a silica gel having a cation-exchange group is carried out by treating in advance a silica gel having a cation-exchange group with a derivatizing agent for a carbonyl compound and then bringing it into contact with an organic solvent containing the derivatizing agent for a carbonyl compound. Specifically, a silica gel having a cation-exchange group is immersed firstly for usually 1 to 2 hours in a solution containing a derivatizing agent for a carbonyl compound, and then filtered followed by drying to obtain a silica gel having an organic ion-exchange group treated with the derivatizing agent for a carbonyl compound. Subsequently, the obtained silica gel having an organic ion-exchange group treated with a derivatizing agent for a carbonyl compound is filled in a container such as a cartridge column and then an organic solvent containing the derivatizing agent for a carbonyl compound is filled in the container and if necessary further flowed usually therethrough in an amount of usually 5 to 20 mL, preferably 5 to 10 mL at a rate of usually 1 to 20 mL/minute for 1 to 20 minutes and then a gas such as nitrogen gas and air is blown to discharge an excess organic solvent followed by drying to obtain a silica gel supporting the derivatizing agent for a carbonyl compound.

In the above production method, the concentration of a derivatizing agent for a carbonyl compound in the solution containing the derivatizing agent for a carbonyl compound to be used for treating in advance a silica gel having a cation-exchange group is usually 0.02 to 0.4 mg/mL, preferably 0.2 to 0.4 mg/mL. The solvent to be used for preparing the solution to be used is preferably, for example, water, methanol, ethanol and acetonitrile, and among these, water is particularly preferable.

In the above production method, the derivatizing agent for a carbonyl compound to be used for treating in advance a silica gel having a cation-exchange group may be a purified one or a crude one, but the derivatizing agent for a carbonyl compound to be used for contacting afterward is preferably a purified one. The purification method may be a known method, for example, a recrystallization method. In addition, specific examples of the derivatizing agent for a carbonyl compound include the one described in the above paragraph on the derivatizing agent for a carbonyl compound related to the present invention. The organic solvent of an organic solvent containing a derivatizing agent for a carbonyl compound includes the same one as the above specific examples.

In the above production method, the container to be used for bringing a silica gel having a cation-exchange group treated in advance with a derivatizing agent for a carbonyl compound into contact with an organic solvent containing the derivatizing agent for a carbonyl compound is preferably a sealed container to be used in the method for producing a silica gel supporting a derivatizing agent for a carbonyl compound of the present invention using the above acid-supported silica gel. The gas such as air and nitrogen gas to be blown into the container after bringing a silica gel having a cation-exchange group into contact with an organic solvent containing a derivatizing agent for a carbonyl compound is preferably the one from which carbonyl compounds are removed. In addition, the removing method may be similar to the method described in the above production method.

In the above production method, the concentration of a derivatizing agent for a carbonyl compound in an organic solvent containing the derivatizing agent for a carbonyl compound and the amount of the organic solvent containing the derivatizing agent for a carbonyl compound may be set according to the values described in the method for producing a silica gel supporting a derivatizing agent for a carbonyl compound of the present invention. Drying in the above production method may be carried out according to the method described in the method for producing a silica gel supporting a derivatizing agent for a carbonyl compound of the present invention.

A more specific method for producing a silica gel supporting a derivatizing agent for a carbonyl compound using a silica gel having a cation-exchange group will be described in detail as follows, taking as an example the case where 2,4-DNPH is used as a derivatizing agent for a carbonyl compound and acetonitrile is used as an organic solvent.

Namely, first, a silica gel having a cation-exchange group is immersed for usually 1 to 2 hours in an aqueous solution of a derivatizing agent for a carbonyl compound of the above described concentration and then filtered, and dried at usually 10 to 50° C., under reduced pressure if necessary. Subsequently, a cartridge column is filled with 0.5 to 1 g of the obtained silica gel having an organic ion-exchange group treated with a derivatizing agent for a carbonyl compound, and then usually 5 to 20 mL, preferably 5 to 10 mL of acetonitrile containing 2,4-DNPH is filled in the cartridge column and further flowed usually at a rate of 1 to 20 mL/minute for 1 to 20 minutes therethrough. Afterward, nitrogen gas or the like is blown to discharge excess acetonitrile and then the silica gel in the cartridge column is dried at usually 10 to 50° C., under reduced pressure if necessary, to obtain a 2,4-DNPH supported silica gel, that is, a silica gel supporting a derivatizing agent for a carbonyl compound of the present invention. In addition, the nitrogen gas or the like to be used here is preferably a gas that has passed through a column for collecting carbonyl compounds.

The present invention will be described in more detail with reference to the following examples, however, to which the present invention is not limited.

Example 1

Production of a Cartridge Column Filled with a Silica Gel Supporting 2,4-DNPH Using Metaphosphoric Acid as an Acid [1]

After 10 g of crushed silica gel (Wakogel C-200 (manufactured by Wako Pure Chemical Industries, Ltd.), particle size: 75 to 150 μm) was put into a glass container, an aqueous solution dissolving 2.5 g of metaphosphoric acid (manufactured by Wako Pure Chemical Industries, Ltd.) in 5 mL of ion-exchange water was added into the container with divided into three portions while being mixed for one hour using a rotary mixer. Then, the content was then heated and dried under reduced pressure to obtain 12.0 g of a metaphosphoric acid-supported silica gel, of which 0.7 g was filled in a polyethylene cartridge column of 10 mm in inside diameter and 17 mm in length. In addition, in a glass container connectable with pipes, 0.038 g of 2,4-DNPH (recrystallized product) recrystallized (purified) in acetonitrile (manufactured by Wako Pure Chemical Industries, Ltd.) for aldehyde analysis as a solvent was dissolved in 30 mL of acetonitrile for aldehyde analysis. In addition, the glass container connectable with pipes is a container that can be connected with pipes both at the inlet and outlet thereof so as to discharge a solution in the container at the outlet by introducing air and the like using a pump at the inlet. A similar glass container connectable with pipes is used in the following examples.

Then, a DNPH-silica cartridge (manufactured by Wako Pure Chemical Industries, Ltd.) to serve as an absorbing tube for carbonyl compounds, the glass container connectable with pipes filled with acetonitrile containing the above 2,4-DNPH and the cartridge column filled with the above metaphosphoric acid supported silica gel were connected via pipes in the above described order. Afterward, air was blown through the DNPH-silica cartridge into the glass container connectable with pipes to push out 10 mL of the acetonitrile solution containing 2,4-DNPH in the glass container at a rate of 10 mL/minute. The acetonitrile solution was filled in the cartridge column filled with a metaphosphoric acid supported silica gel and then flowed therethrough. After flowing the solution, an excess solution in the cartridge column was discharged by $N_2$ gas that passed through the DNPH-silica cartridge followed by drying at room temperature under reduced pressure to obtain a cartridge column 1 filled with a 2,4-DNPH supported silica gel.

Example 2

Production of a Cartridge Column Filled with a 2,4-DNPH Supported Silica Gel Using Metaphosphoric Acid as an Acid [2]

After 10 g of crushed silica gel (Wakogel C-200 (manufactured by Wako Pure Chemical Industries, Ltd.), particle size: 75 to 150 μm) was put in a glass container, an aqueous solution dissolving 0.0025 g of 2,4-dinitrophenylhydrazine (2,4-DNPH) (manufactured by Wako Pure Chemical Industries, Ltd.) and 2.5 g of metaphosphoric acid (manufactured by Wako Pure Chemical Industries, Ltd.) in 5 mL of ion-exchange water was poured to the container with divided into three portions while being mixed for one hour using a rotary mixer. The content was then heated and dried under reduced pressure to obtain 12.0 g of a metaphosphoric acid supported silica gel treated with 2,4-DNPH, of which 0.7 g was filled in a polyethylene cartridge column of 10 mm in inside diameter and 17 mm in length.

In a glass container connectable with pipes, 0.038 g of 2,4-DNPH (recrystallized product) recrystallized in acetonitrile (manufactured by Wako Pure Chemical Industries, Ltd.) for aldehyde analysis as a solvent was dissolved in 30 mL of acetonitrile for aldehyde analysis. Similarly as in Example 1, the above acetonitrile solution containing 2,4-DNPH was flowed through the cartridge column followed by drying to obtain a cartridge column 2 filled with a 2,4-DNPH supported silica gel.

Example 3

Production of a Cartridge Column Filled with a 2,4-DNPH Supported Silica Gel Using Boric Acid as an Acid After 10 g of crushed silica gel (Wakogel C-200 (manufactured by Wako Pure Chemical Industries, Ltd.), particle size: 75 to 150 μm) was put in a glass container, an aqueous solution dissolving 0.0025 g of 2,4-DNPH (manufactured by Wako Pure Chemical Industries, Ltd.) and 0.24 g of boric acid (manufactured by Wako Pure Chemical Industries, Ltd.) in 5 mL of ion-exchange water was poured to the container with divided into three portions while being mixed for one hour using a rotary mixer. The content was then heated and dried under reduced pressure to obtain 10.3 g of a silica gel-supported boric acid treated with 2,4-DNPH, of which 0.7 g was filled in a polyethylene cartridge column of 10 mm in inside diameter and 17 mm in length. In a glass container connectable with pipes 0.038 g of 2,4-DNPH (recrystallized product) recrystallized in acetonitrile (manufactured by Wako Pure Chemical Industries, Ltd.) for aldehyde analysis as a solvent was dissolved in 30 mL of acetonitrile for aldehyde analysis.

Then, a DNPH silica cartridge (manufactured by Wako Pure Chemical Industries, Ltd.) to serve as an absorbing tube for carbonyl compounds, the glass container connectable with pipes filled with acetonitrile containing the above 2,4-DNPH and the cartridge column filled with a boric acid supported silica gel supported the above 2,4-DNPH were connected via pipes in the above described order. Afterward, air was blown through the DNPH-silica cartridge into the glass container connectable with pipes to push out the acetonitrile solution containing 2,4-DNPH in the glass container at a rate of 10 mL/minute. The acetonitrile solution was filled in the cartridge column filled with a boric acid supported silica gel and then flowed therethrough. After flowing the solution, an excess solution in the cartridge column was discharged by $N_2$ gas that passed through the DNPH-silica cartridge followed by drying at room temperature under reduced pressure to obtain a cartridge column 3 filled with a 2,4-DNPH supported silica gel.

Example 4

Production of a Cartridge Column Filled with a 2,4-DNPH Supported Silica Gel Using Tartaric Acid as an Acid After 10 g of crushed silica gel (Wakogel C-200 (manufactured by Wako Pure Chemical Industries, Ltd.), particle size: 75 to 150 μm) was put in a glass container, an aqueous solution dissolving 0.0025 g of 2,4-DNPH (manufactured by Wako Pure Chemical Industries, Ltd.) and 0.87 g of tartaric acid (manufactured by Wako Pure Chemical Industries, Ltd.) in 5 mL of ion-exchange water was poured to the container with divided into three portions while being mixed for one hour using a rotary mixer. The content was then heated and dried under reduced pressure to obtain 11.0 g of a tartaric acid supported silica gel treated with 2,4-DNPH, of which 0.9 g was filled in a polyethylene cartridge column of 10 mm in inside diameter and 17 mm in length. Also, in a glass container connectable with pipes, 0.038 g of 2,4-DNPH (recrystallized product) recrystallized in acetonitrile (manufactured by Wako Pure Chemical Industries, Ltd.) for aldehyde analysis as a solvent was dissolved in 30 mL of acetonitrile for aldehyde analysis.

Then, a DNPH-silica cartridge (manufactured by Wako Pure Chemical Industries, Ltd.) to serve as an absorbing tube for carbonyl compounds, the glass container connectable with pipes filled with acetonitrile containing the above 2,4-DNPH and the cartridge column filled with the above tartaric acid supported silica gel were connected via pipes in the above described order. Afterward, air was blown through the DNPH-silica cartridge into the glass container connectable with pipes to push out the acetonitrile solution containing 2,4-DNPH in the glass container at a rate of 10 mL/minute. The acetonitrile solution was filled in the cartridge column filled with a tartaric acid supported silica gel and then flowed therethrough. After flowing the solution, an excess solution in the cartridge column was discharged by $N_2$ gas that passed through the DNPH silica cartridge followed by drying at room temperature under reduced pressure to obtain a cartridge column 4 filled with a 2,4-DNPH supported silica gel.

Example 5

Production of a Cartridge Column Filled with a 2,4-DNPH Supported Silica Gel Using Sulfamic Acid as an Acid After 10 g of crushed silica gel (Wakogel C-200 (manufactured by Wako Pure Chemical Industries, Ltd.), particle size: 75 to 150 μm) was put in a glass container, an aqueous solution dissolving 0.0025 g of 2,4-DNPH (manufactured by Wako Pure Chemical Industries, Ltd.) and 0.56 g of sulfamic acid (manufactured by Wako Pure Chemical Industries, Ltd.) in 5 mL of ion-exchange water was poured to the container with divided into three portions while being mixed for one hour using a rotary mixer. The content was then heated and dried under reduced pressure to obtain 10.5 g of sulfamic acid supported silica gel treated with 2,4-DNPH, of which 0.7 g was filled in a polyethylene cartridge column of 10 mm in inside diameter and 17 mm in length. In a glass container connectable with pipes 0.038 g of 2,4-DNPH (recrystallized product) recrystallized in acetonitrile (manufactured by Wako Pure Chemical Industries, Ltd.) for aldehyde analysis as a solvent was dissolved in 30 mL of acetonitrile for aldehyde analysis.

Then, a DNPH-silica cartridge (manufactured by Wako Pure Chemical Industries, Ltd.) to serve as an absorbing tube for carbonyl compounds, the glass container connectable with pipes filled with acetonitrile containing the above 2,4-DNPH and the above cartridge column filled with the above sulfamic acid supported silica gel were connected via pipes in the above described order. Afterward, air was blown through the DNPH silica cartridge into the glass container connectable with pipes to push out the acetonitrile solution containing 2,4-DNPH in the glass container at a rate of 10 mL/minute. The acetonitrile solution was filled in the cartridge column filled with a sulfamic acid supported silica gel and then flowed therethrough. After flowing the solution, an excess solution in the cartridge column was discharged by $N_2$ gas that passed through the DNPH silica cartridge followed by drying at room temperature under reduced pressure to obtain a cartridge column 5 filled with a 2,4-DNPH supported silica gel.

Example 6

Production of a Cartridge Column Filled with a 2,4-DNPH Supported Silica Gel Using a Silica Gel Having Carboxylic Acid as an Ion-Exchange Group 10 g of carboxylic acid-bonded crushed silica gel (manufactured by J.T. Baker Inc., average particle size: 50 μm) and 100 mL of 0.1 mol/L aqueous solution of hydrochloric acid were mixed and then left for standing for one hour. The mixture was filtered with a glass funnel in a degree such as not to allow drying and then subjected to washing with 100 mL of ion-exchange water and filtration each repeated three times. The mixture was then heated and dried under reduced pressure to obtain 9.7 g of an $H^+$-type carboxylic acid-bonded silica gel.

The obtained 9.7 g of $H^+$-type carboxylic acid-bonded silica gel was put in a glass container and then an aqueous solution dissolving 0.0025 g of 2,4-DNPH (manufactured by Wako Pure Chemical Industries, Ltd.) in 5 mL of ion-exchange water was poured to the container with divided into three portions while being mixed for one hour using a rotary mixer. The content was then heated and dried under reduced pressure to obtain 9.8 g of carboxylic acid supported silica gel treated with 2,4-DNPH, of which 0.7 g was filled in a polyethylene cartridge column of 10 mm in inside diameter and 17 mm in length. Also, in a glass container connectable with pipes, 0.038 g of 2,4-DNPH (recrystallized product) recrystallized in acetonitrile (manufactured by Wako Pure Chemical Industries, Ltd.) for aldehyde analysis as a solvent was dissolved in 30 mL of acetonitrile for aldehyde analysis.

Then, A DNPH-silica cartridge (manufactured by Wako Pure Chemical Industries, Ltd.) to serve as an absorbing tube for carbonyl compounds, the glass container connectable with pipes filled with acetonitrile containing the above 2,4-DNPH and the cartridge column filled with the above carboxylic acid-bonded silica gel were connected via pipes in the above described order. Afterward, air was blown through the DNPH-silica cartridge into the glass container connectable with pipes to push out 10 mL of acetonitrile solution containing 2,4-DNPH in the glass container at a rate of 10 mL/minute. The acetonitrile solution was filled in the cartridge column filled with the carboxylic acid-bonded silica gel and then flowed therethrough. After flowing the solution, an excess solution in the cartridge column was discharged by $N_2$ gas that passed through the DNPH-silica cartridge followed by drying at room temperature under reduced pressure to obtain a cartridge column 6 filled with a 2,4-DNPH supported silica gel.

Example 7

Production of a Cartridge Column Filled with a 2,4-DNPH Supported Silica Gel Using a Silica Gel Having Sulfonic Acid as an Ion-Exchange Group 10 g of sulfonic acid-bonded crushed silica gel (manufactured by J.T. Baker Inc., average particle size: 40 µm) and 100 mL of 0.1 mol/L aqueous solution of hydrochloric acid were mixed and then left for standing for one hour. The mixture was filtered with a glass funnel in a degree such as not to allow drying and then subjected to washing with 100 mL of ion-exchange water and filtration each repeated three times. The mixture was then heated and dried under reduced pressure to obtain 9.1 g of an $H^+$-type sulfonic acid-bonded silica gel.

The obtained 9.1 g of the $H^+$-type sulfonic acid-bonded silica gel was put in a glass container and then an aqueous solution dissolving 0.0025 g of 2,4-DNPH (manufactured by Wako Pure Chemical Industries, Ltd.) in 5 mL of ion-exchange water was poured to the container with divided into three portions while being mixed for one hour using a rotary mixer. The content was then heated and dried under reduced pressure to obtain 9.4 g of sulfonic acid supported silica gel treated with 2,4-DNPH, of which 0.7 g was filled in a polyethylene cartridge column of 10 mm in inside diameter and 17 mm in length. Also, 0.038 g of 2,4-DNPH (recrystallized product) recrystallized in acetonitrile (manufactured by Wako Pure Chemical Industries, Ltd.) for aldehyde analysis as a solvent was dissolved in 30 mL of acetonitrile for aldehyde analysis in a glass container connectable with pipes.

Then, A DNPH-silica cartridge (manufactured by Wako Pure Chemical Industries, Ltd.) to serve as an absorbing tube for carbonyl compounds, the above glass container connectable with pipes filled with acetonitrile containing 2,4-DNPH and the above cartridge column filled with the sulfonic acid-bonded silica gel were connected via pipes in the above described order. Afterward, air was blown through the DNPH-silica cartridge into the glass container connectable with pipes to push out 10 mL of the acetonitrile solution containing 2,4-DNPH in the glass container at a rate of 10 mL/minute. The acetonitrile solution was filled in the cartridge column filled with the sulfonic acid-bonded silica gel and then flowed therethrough. After flowing the solution, an excess solution in the cartridge column was discharged by $N_2$ gas that passed through the DNPH-silica cartridge followed by drying at room temperature under reduced pressure to obtain a cartridge column 7 filled with a 2,4-DNPH supported silica gel.

Example 8

Production of a Cartridge Column Filled with a 2,4-DNPH Supported Silica Gel Using Metaphosphoric Acid as an Acid [3]

After 10 g of crushed silica gel (Wakogel C-100 (manufactured by Wako Pure Chemical Industries, Ltd.), particle size: 150 to 450 µm) was put in a glass container, an aqueous solution dissolving 0.0025 g of 2,4-dinitrophenylhydrazine (2,4-DNPH) (manufactured by Wako Pure Chemical Industries, Ltd.) and 2.5 g of metaphosphoric acid (manufactured by Wako Pure Chemical Industries, Ltd.) in 5 mL of ion-exchange water was poured to the container with divided into three portions while being mixed for one hour using a rotary mixer. The content was then heated and dried under reduced pressure to obtain 12.0 g of a metaphosphoric acid supported silica gel treated with 2,4-DNPH, of which 0.35 g was filled in a polyethylene cartridge column of 10 mm in inside diameter and 9 mm in inside length.

Also, 0.019 g of 2,4-DNPH (recrystallized product) recrystallized in acetonitrile (manufactured by Wako Pure Chemical Industries, Ltd.) for aldehyde analysis as a solvent was dissolved in 15 mL of acetonitrile for aldehyde analysis in a glass container connectable with pipes. Then, similarly as in Example 1, the acetonitrile solution containing the 2,4-DNPH was flowed through the cartridge column followed by drying to obtain a cartridge column 8 filled with a 2,4-DNPH supported silica gel.

Example 9

Measurement of the Cartridge Blank Value and Lower Limit of Determination for Formaldehyde (1) Preparation of a Formaldehyde Standard Solution A solution prepared by diluting an acetonitrile solution containing a formaldehyde-2,4-DNPH derivative (100 µg/mL, manufactured by Sigma-Aldrich Corporation) with Wako's acetonitrile for aldehyde analysis to 10 µg/mL was used as a formaldehyde standard solution. The standard solution was diluted stepwise and injected into a high-performance liquid chromatography (HPLC) to draw a calibration curve for formaldehyde using the obtained peak areas. The conditions of HPLC are as follows:

(HPLC Conditions)

column: WSII5C18RS (4.6×250 mm, manufactured by Wako Pure Chemical Industries, Ltd.), mobile phase: 60% aqueous solution of acetonitrile, flow rate: 1.0 mL/min, column temperature: 40° C., detection: UV detection, measuring wavelength: 360 nm (2) Measurement of the Blank Value Acetonitrile (manufactured by Wako Pure Chemical Industries, Ltd.) for aldehyde analysis was flowed at a rate of about 1.7 mL/minute through each of the cartridge columns 1 to 8 obtained in Examples 1 to 8 to obtain the first 5 mL of the flowed acetonitrile, of which 10 μL was injected into a high-performance liquid chromatography (HPLC). As a reference example, 10 μL of acetonitrile prepared by similar operations using Sep-Pak DNPH-silica (manufactured by Waters Corporation) as a cartridge column was injected into a high-performance liquid chromatography (HPLC). Peak areas for formaldehyde were determined from each chromatogram to calculate each concentration using the calibration curve obtained in (1). The obtained concentration (μg/mL) was then multiplied by the dose (5 mL) of the cartridge column to calculate the blank value for one cartridge (cartridge blank value, μg/Cart.) The obtained cartridge blank values for formaldehyde are shown in Table 1. The cartridge blank value is an average value of the values measured and calculated each using 3 columns per each of the cartridge columns 1 to 8 prepared according to the methods described in Examples 1 to 8 or 3 columns of Sep-Pak DNPH-silica.

Also, the standard deviations (s) of ambient concentration for 3 columns per each cartridge of the cartridge columns 1 to 8 and 3 columns of Sep-Pak DNPH-silica were calculated from the obtained cartridge blank value for each component using the conversion equation for aldehyde concentration in the outdoor/indoor air given in the manual for measuring hazardous air pollutants (Environment Ministry, February 1997). The lower limit of determination was defined as a value obtained by multiplying the above standard deviation by 10. The lower limit of determination also serves as an index for scattering of the blank value. Specifically, calculations were carried out as follows:

Namely, the obtained cartridge blank value for each aldehyde compound of each cartridge column was used to calculate each ambient concentration (μg/m$^3$) by equation 1 below. Further, the standard deviations (s) of ambient concentration of three cartridges (n=3) were used to calculate the lower limit of determination for each blank component by equation 2 below. The obtained lower limits of determination are shown in Table 1.

$$C=(A\times E\times 1000)/(v\times V\times 293/(273+t)\times P/101.3) \quad \text{Equation 1}$$

C: concentration (μg/m$^3$) of each aldehyde in the air at 20° C.
A: cartridge blank value (ng)
  [weight of each blank component contained in 10 μL of the sample injected into HPLC]
E: amount of test liquid (mL) [amount of extract=5 mL]
v: injected amount into HPLC (μL) [v=10 μL]
V: collected amount measured with a gas meter (L) [L=144 L is set]
t: average temperature when samples are collected (° C.) [t=20° C. is set]
P: average atmospheric pressure when samples are collected (kPa) [P=101.3 is set]

$$\text{lower limit of determination}=10\ s(\mu g/m^3) \quad \text{Equation 2}$$

TABLE 1

| Column Number (acid catalyst or ion-exchange group) | Formaldehyde | |
|---|---|---|
| | Cartridge Blank Value | Lower Limit of Determination |
| Cartridge Column 1 (no DNPH treatment in advance, metaphosphoric acid) | 0.023 | 0.290 |
| Cartridge Column 2 (metaphosphoric acid) | 0.015 | 0.164 |
| Cartridge Column 3 (boric acid) | 0.035 | 0.099 |
| Cartridge Column 4 (tartaric acid) | 0.033 | 0.077 |
| Cartridge Column 5 (sulfamic acid) | 0.051 | 0.286 |
| Cartridge Column 6 (carboxylic acid) | 0.048 | 0.032 |
| Cartridge Column 7 (sulfonic acid) | 0.022 | 0.318 |
| Cartridge Column 8 (metaphosphoric acid) | 0.011 | 0.100 |
| Sep-Pak DNPH-silica Gel (Reference Example) | 0.060 | 0.565 |

As apparent from the results shown in Table 1, it was found that all of cartridge blank values and lower limits of determination for formaldehyde of the cartridge columns of the present invention were lower compared with those of Sep-Pak DNPH-silica gel of a conventional cartridge column.

It was also found that when cartridge column 2 treated in advance with DNPH was compared with cartridge column 1 not treated, the treated cartridge column 2 of which the cartridge blank value and the lower limit of determination were lower was more suitable for high-sensitivity analysis.

Example 10

Measurement of the Cartridge Blank Value and Lower Limit of Determination for Acetaldehyde (1) Preparation of an Acetaldehyde Standard Solution A solution prepared by diluting an acetaldehyde-2,4-DNPH derivative (1,000 μg/mL, manufactured by Sigma-Aldrich Corporation) with Wako's acetonitrile for aldehyde analysis to 10 μg/mL was used as an acetaldehyde standard solution. The standard solution was diluted stepwise and injected into a high-performance liquid chromatography (HPLC) to draw a calibration curve for acetaldehyde using the obtained peak areas. The conditions of HPLC are the same as in Example 9 (1).

(2) Measurement of the Blank Value and Lower Limit of Determination

Chromatograms were obtained by similar operation as in Example 9 (2) using cartridge columns 2, 4, 7 and 8 and Sep-Pak DNPH-silica (manufactured by Waters Corporation) as a cartridge column. Peak areas for acetaldehyde were determined from the chromatograms to calculate each concentration using the calibration curve obtained in (1). The obtained concentration (μg/mL) was then multiplied by the dose (5 mL) of the cartridge column to calculate the blank value for acetaldehyde for one cartridge (cartridge blank value, μg/Cart.). The obtained cartridge blank values for acetaldehyde are shown in Table 2. The cartridge blank value is an average value of the values measured and calculated each using 3 columns per each of the cartridge columns 2, 4, 7 and 8 prepared according to the methods described in Examples 2, 4, 7 and 8 or 3 columns of Sep-Pak DNPH-silica. The lower limit of determination for acetaldehyde was calculated similarly as in Example 8-9 (2) from the obtained cartridge blank value for each component. The obtained values are shown in Table 2.

TABLE 2

| Column Number | Acetaldehyde | |
|---|---|---|
| (acid catalyst or ion-exchange group) | Cartridge Blank Value | Lower Limit of Determination |
| Cartridge Column 2 (metaphosphoric acid) | 0.007 | 0.083 |
| Cartridge Column 4 (tartaric acid) | 0.042 | 0.134 |
| Cartridge Column 7 (sulfonic acid) | 0.055 | 0.124 |
| Cartridge Column 8 (metaphosphoric acid) | 0.008 | 0.039 |
| Sep-Pak DNPH-silica Gel (Reference Example) | 0.149 | 0.122 |

From the results shown in Table 2, it was found that the cartridge blank values for acetaldehyde of the cartridge columns of the present invention were lower compared with that of Sep-Pak DNPH-silica gel of a conventional column, and the lower limits of determination of the cartridge columns of the present invention were also similar to or lower than that of the conventional cartridge column. It was shown, therefore, that the cartridge column of the present invention was more excellent as a column for determination of acetaldehyde than conventional columns.

Example 11

Measurement of the Cartridge Blank Value and Lower Limit of Determination for Acetone (1) Preparation of an Acetone Standard Solution A solution prepared by diluting an acetone-2,4-DNPH derivative (1,000 μg/mL, manufactured by Sigma-Aldrich Corporation) with Wako's acetonitrile for aldehyde analysis to 10 μg/mL was used as an acetone standard solution. The standard solution was diluted stepwise and injected into a high-performance liquid chromatography (HPLC) to draw a calibration curve for acetone using the obtained peak areas. The conditions of HPLC are the same as in Example 9 (1).

(2) Measurement of the Blank Value and Lower Limit of Determination

Chromatograms were obtained by similar operation as in Example 9 (2) using cartridge columns 2, 3 and 8 and Sep-Pak DNPH-silica (manufactured by Waters Corporation) as a cartridge column. Peak areas for acetone were determined from the chromatograms to calculate each concentration using the calibration curve obtained in (1). The obtained concentration (μg/mL) was then multiplied by the dose (5 mL) of the cartridge column to calculate the blank value for acetone for one cartridge (cartridge blank value, μg/Cart.). The obtained cartridge blank values for acetone are shown in Table 3. The cartridge blank value is an average value of the values measured and calculated each using 3 columns per each of the cartridge columns 2, 3 and 8 prepared according to the methods described in Examples 2, 3 and 8 or 3 columns of Sep-Pak DNPH-silica. The lower limit of determination for acetone was calculated similarly as in Example 9 (2) from the obtained cartridge blank value for each component. The obtained values are shown in Table 3.

TABLE 3

| Column Number | Acetone | |
|---|---|---|
| (acid catalyst or ion-exchange group) | Cartridge Blank Value | Lower Limit of Determination |
| Cartridge Column 2 (metaphosphoric acid) | 0.018 | 0.132 |
| Cartridge Column 3 (boric acid) | 0.051 | 0.096 |
| Cartridge Column 8 (metaphosphoric acid) | 0.011 | 0.049 |
| Sep-Pak DNPH-silica Gel (Reference Example) | 0.121 | 0.122 |

From the results shown in Table 3, it was found that the cartridge blank values for acetone of the cartridge columns of the present invention were lower compared with that of Sep-Pak DNPH-silica, a conventional column, and the lower limits of determination of the cartridge columns of the present invention were also similar to or lower than that of the conventional cartridge column. It was shown, therefore, that the cartridge column of the present invention was more excellent as a column for determination of acetone than conventional columns.

Example 12

Measurement of Recovery Rates of Added Formaldehyde and Acetaldehyde (1) Preparation of Standard Solutions of Formaldehyde and Acetaldehyde A solution prepared by diluting a formaldehyde solution (37%, manufactured by Wako Pure Chemical Industries, Ltd.) by 1,000-fold with Wako's acetonitrile for aldehyde analysis was used as a standard solution of formaldehyde. A solution prepared by diluting acetaldehyde (99%, manufactured by Sigma-Aldrich Corporation) by 2,000-fold with Wako's acetonitrile for aldehyde analysis was used as a standard solution of acetaldehyde.

(2) Addition of the Standard Solutions to Prototype Cartridges by $N_2$ Gas Purge A commercially available cartridge column for collecting carbonyl compounds, a sample-injecting tube and cartridge column 2 of the present invention were connected in series via pipes to the outlet of a $N_2$ gas bomb. After $N_2$ gas was filled in the system, the above standard solutions of formaldehyde and acetaldehyde of each 8 μL were injected through the sample-injecting tube and then $N_2$ gas was blown at a rate of 1 L/minute for about 10 minutes. After completion of blowing, the cartridge column was detached from the system, sealed with a cap and left for standing at room temperature for about 2 hours. Acetonitrile (manufactured by Wako Pure Chemical Industries, Ltd.) for aldehyde analysis was then flowed at a rate of about 1.7 mL/minute and the first 5 mL of the flowed acetonitrile was obtained, of which 10 μL was injected in a high-performance liquid chromatography (HPLC) to measure peak areas for formaldehyde and acetaldehyde. Similar measurements were carried out with cartridge columns 3 to 7. The conditions of HPLC were the same as those in Example 9 (1) and the peak area was compensated for the blank value in measurement.

(3) Addition of the Standard Solutions to a Mixed Solution of Phosphoric Acid and DNPH After recrystallized DNPH of 2 mg and 100 μL of phosphoric acid (manufactured by Wako Pure Chemical Industries, Ltd.) were put in a 5 mL glass measuring flask, 4 mL of acetonitrile (manufactured by Wako Pure Chemical Industries, Ltd.) for aldehyde analysis is added and then mixed in a ultrasonic water tank to completely dissolve the recrystallized DNPH. To this mixed solution each 8 μL of the above standard solutions of formaldehyde and acetaldehyde is added and then left for standing at room temperature for about 2 hours. The above solution of 10 μL was injected into HPLC. The conditions of HPLC were the same as those in (2) and the peak area was compensated for the blank value in measurement.

(4) Calculation of the Addition Recovery Rate

The addition recovery rate was calculated by setting each amount of formaldehyde and acetaldehyde collected in (3) at 100. Specifically, the addition recovery rates were calculated from the peak areas of formaldehyde and acetaldehyde measured in (2) and (3) using the following equation. The calculated results are shown in Table 4.

Addition recovery rate(%)=Peak area measured in (2)/Peak area measured in (3)×100

TABLE 4

|  | Addition recovery rate (%) | |
| --- | --- | --- |
|  | Formaldehyde | Acetaldehyde |
| Cartridge Column 2 (metaphosphoric acid) | 96.8 | 98.4 |
| Cartridge Column 3 (boric acid) | 101.3 | 97.9 |
| Cartridge Column 4 (tartaric acid) | 100.9 | 99.6 |
| Cartridge Column 5 (sulfamic acid) | 99.8 | 98.6 |
| Cartridge Column 6 (carboxylic acid | 99.2 | 98.7 |
| Cartridge Column 7 (sulfonic acid) | 103.1 | 94.9 |

As apparent from the results of Table 4, it was found that the column filled with a silica gel supporting a derivatizing agent for a carbonyl compound obtained by the production method of the present invention had similar performance for collecting carbonyl compounds as in conventional collecting methods for carbonyl compounds using a phosphoric acid solution and DNPH.

What is claimed is:

1. A method for producing a silica gel supporting a derivatizing agent for a carbonyl compound, which method comprises (a) providing an acid-supported silica gel that contains an acid which is supported in a solid state, and (b) bringing the acid-supported silica gel into contact with an organic solvent containing the derivatizing agent for a carbonyl compound, wherein the acid is not soluble or is hardly soluble in the organic solvent.

2. The method according to claim 1, wherein the acid-supported silica gel is produced by bringing a silica gel into contact with an aqueous solution in which the acid is dissolved.

3. The method according to claim 1, wherein the acid-supported silica gel is an acid-supported silica gel treated by a derivatizing agent for a carbonyl compound that is treated in advance by the derivatizing agent for a carbonyl compound.

4. The method according to claim 3, wherein the acid-supported silica gel treated by a derivatizing agent for a carbonyl compound is produced by bringing a silica gel into contact with a mixed solution containing the acid and the derivatizing agent for a carbonyl compound.

5. The method according to claim 3, wherein the acid-supported silica gel treated by a derivatizing agent for a carbonyl compound is produced by bringing an acid-supported silica gel into contact with a solution containing the derivatizing agent for a carbonyl compound.

6. The method according to claim 1, wherein the acid is selected from metaphosphoric acid, boric acid, sulfamic acid and tartaric acid.

7. The method according to claim 1, wherein the acid is metaphosphoric acid.

8. The method according to claim 1, wherein the derivatizing agent for a carbonyl compound is dinitrophenylhydrazine.

9. The method according to claim 1, wherein the derivatizing agent for a carbonyl compound is purified.

10. The method according to claim 1, wherein the organic solvent containing a derivatizing agent for a carbonyl compound is acetonitrile.

11. The method according to claim 1, wherein the contact of the acid-supported silica gel and the organic solvent containing a derivatizing agent for a carbonyl compound is carried out in a sealed container.

12. A method for producing a silica gel supporting a derivatizing agent for a carbonyl compound characterized by bringing an acid-supported silica gel treated with the derivatizing agent for a carbonyl compound obtained by bringing a silica gel into contact with a mixed solution of metaphosphoric acid and the derivatizing agent for a carbonyl compound, into contact with an organic solvent containing the derivatizing agent for a carbonyl compound.

* * * * *